(12) United States Patent
MacDonald et al.

(10) Patent No.: US 9,138,386 B2
(45) Date of Patent: Sep. 22, 2015

(54) DENTAL WHITENING COMPOSITIONS

(75) Inventors: Jeff MacDonald, Pomona, CA (US);
Nancy N. Quan, North Hills, CA (US);
Robert Hayman, Los Angeles, CA (US)

(73) Assignee: DISCUS DENTAL, LLC, Culver City, CA (US)

( * ) Notice: Subject to any disclaimer, the term of this patent is extended or adjusted under 35 U.S.C. 154(b) by 0 days.

(21) Appl. No.: 12/947,710

(22) Filed: Nov. 16, 2010

(65) Prior Publication Data
US 2011/0059030 A1 Mar. 10, 2011

Related U.S. Application Data

(63) Continuation of application No. 11/271,412, filed on Nov. 9, 2005, now abandoned.

(60) Provisional application No. 60/626,407, filed on Nov. 9, 2004, provisional application No. 60/631,121, filed on Nov. 26, 2004, provisional application No. 60/646,309, filed on Jan. 22, 2005, provisional application No. 60/653,421, filed on Feb. 15, 2005.

(51) Int. Cl.
A61K 8/24 (2006.01)
A61Q 11/00 (2006.01)
A61K 8/22 (2006.01)
A61C 19/06 (2006.01)
A61K 8/19 (2006.01)
A61K 8/60 (2006.01)

(52) U.S. Cl.
CPC ............. *A61K 8/22* (2013.01); *A61C 19/066* (2013.01); *A61K 8/19* (2013.01); *A61K 8/60* (2013.01); *A61Q 11/00* (2013.01); *A61K 2800/88* (2013.01)

(58) Field of Classification Search
USPC .............................................. 424/49; 514/23
See application file for complete search history.

(56) References Cited

U.S. PATENT DOCUMENTS

| | | |
|---|---|---|
| 4,357,318 A | 11/1982 | Shah et al. |
| 4,592,487 A | 6/1986 | Simmon et al. |
| 4,631,141 A | 12/1986 | Baxter |
| 4,699,623 A | 10/1987 | Dubreux et al. |
| 4,954,316 A | 9/1990 | Globus |
| 5,037,639 A | 8/1991 | Tung |
| 5,128,342 A | 7/1992 | Globus |
| 5,138,520 A | 8/1992 | McMillan et al. |
| 5,165,424 A * | 11/1992 | Silverman ............. 128/861 |
| 5,256,402 A | 10/1993 | Prencipe et al. |
| 5,268,167 A | 12/1993 | Tung |
| 5,434,102 A | 7/1995 | Watanabe et al. |
| 5,437,857 A | 8/1995 | Tung |
| 5,439,845 A | 8/1995 | Watanabe et al. |
| 5,534,244 A | 7/1996 | Tung |
| 5,571,502 A | 11/1996 | Winston |
| 5,599,525 A * | 2/1997 | Hsu et al. .............. 424/49 |
| 5,624,906 A * | 4/1997 | Vermeer ................ 514/23 |
| 5,645,428 A | 7/1997 | Yarborough |
| 5,648,064 A | 7/1997 | Gaffar et al. |
| 5,770,105 A | 6/1998 | Fischer |
| 5,819,988 A | 10/1998 | Sawhney et al. |
| 5,849,267 A | 12/1998 | Collins et al. |
| 5,858,332 A | 1/1999 | Jensen et al. |
| 5,895,641 A | 4/1999 | Winston |
| 5,922,307 A | 7/1999 | Montgomery |
| 5,928,628 A | 7/1999 | Pellico |
| 5,975,906 A | 11/1999 | Knutson |
| 6,000,341 A | 12/1999 | Tung |
| 6,036,944 A | 3/2000 | Winston et al. |
| 6,056,930 A | 5/2000 | Tung |
| 6,065,645 A | 5/2000 | Sawhney et al. |
| 6,155,832 A | 12/2000 | Wiesel |
| 6,159,448 A | 12/2000 | Winston |
| 6,162,055 A | 12/2000 | Montgomery et al. |
| 6,213,671 B1 | 4/2001 | Chang |
| 6,287,120 B1 | 9/2001 | Wiesel |
| 6,312,670 B1 | 11/2001 | Montgomery |
| 6,322,773 B1 | 11/2001 | Montgomery |
| 6,331,292 B1 | 12/2001 | Montgomery |
| 6,343,933 B1 | 2/2002 | Montgomery et al. |
| 6,368,576 B1 | 4/2002 | Jensen et al. |
| 6,416,319 B1 | 7/2002 | Cipolla |
| 6,458,340 B1 | 10/2002 | Ibsen et al. |
| 6,485,708 B1 | 11/2002 | Winston |
| 6,488,914 B2 | 12/2002 | Montgomery |

(Continued)

FOREIGN PATENT DOCUMENTS

| | | |
|---|---|---|
| DE | 1617430 | 4/1972 |
| DE | 10212520 | 10/2003 |
| EP | 0202359 | 11/1986 |
| EP | 0839517 | 5/1998 |
| EP | 1072323 | 4/2000 |
| EP | 1192933 | 4/2002 |
| GB | 1408922 | 10/1972 |
| WO | 96/002624 | 2/1996 |
| WO | 01/70178 | 9/2001 |

OTHER PUBLICATIONS

Giniger et al: "The Clinical Performance of Professionally Dispensed Bleaching Gel With Added Amorphous Calcium Phosphate"; Jada, vol. 136, Mar. 2005, pp. 383-392.

*Primary Examiner* — Walter Webb

(57) ABSTRACT

A two-component whitening system has a de-sensitizing effect as well as re-mineralizing capability. The system may be an unfoamed, a foamed or a foamable composition.

The system has a first component with at least one peroxide compound, at least one source of phosphate and at least one gelling agent; and a second component with at least one source of calcium, strontium and/or mixtures thereof. The second component may also contain at least one gelling agent, and the composition maybe present as a foam or is foamable.

The composition may be packed in a two-compartment syringe.

24 Claims, No Drawings

(56) References Cited

U.S. PATENT DOCUMENTS

| | | |
|---|---|---|
| 6,514,543 B2 | 2/2003 | Montgomery |
| 6,533,582 B2 | 3/2003 | Lindquist |
| 6,536,628 B2 | 3/2003 | Montgomery |
| 6,949,240 B2 | 9/2005 | Sagel et al. |
| 6,958,144 B2 | 10/2005 | Montgomery |
| 2001/0021374 A1 | 9/2001 | Montgomery |
| 2002/0137001 A1 | 9/2002 | Cipolla et al. |
| 2002/0141951 A1 | 10/2002 | Montgomery |
| 2002/0146666 A1 | 10/2002 | Sagel et al. |
| 2003/0089886 A1 | 5/2003 | Montgomery |
| 2003/0198605 A1 | 10/2003 | Montgomery |
| 2004/0101497 A1 | 5/2004 | Montgomery |
| 2005/0008582 A1 | 1/2005 | Du-Thumm et al. |
| 2005/0084826 A1 | 4/2005 | Pilaro et al. |
| 2005/0249679 A1 | 11/2005 | Cameron et al. |
| 2005/0265933 A1 | 12/2005 | Montgomery et al. |

\* cited by examiner

DENTAL WHITENING COMPOSITIONS

CROSS-REFERENCE TO RELATED APPLICATIONS

This application is a continuation of application Ser. No. 11/271,412, filed on Nov. 9, 2005 now abandoned, which claims the benefit of U.S. Provisional patent application Ser. No. 60/626,407, filed Nov. 9, 2004, entitled "Tooth Whitening Compositions"; 60/631,121, filed Nov. 26, 2004, entitled "Whitening System"; 60/646,309, filed Jan. 22, 2005 entitled "Dental Whitening"; and 60/653,421, filed Feb. 15, 2005, entitled "Whitening System Capable of Effective Whitening Action"; the contents of which are hereby incorporated by reference.

FIELD OF THE INVENTION

The present invention relates to improvements in tooth treatment compositions. In particular, this invention relates to whitening compositions.

BACKGROUND OF THE INVENTION

A tooth is comprised of an inner dentin layer and an outer hard enamel that is coated with a protective layer called the acquired pellicle. The enamel layer is composed of hydroxyapatite crystals that create a somewhat porous surface. The pellicle or the enamel can become stained or discolored. It is believed that the porous nature of the enamel layer is what allows staining agents and discoloring substances to permeate the enamel and discolor the tooth.

Many substances that a person's teeth confront or come in contact with on a daily basis can "stain" or reduce the "whiteness" of one's teeth. In particular, food products, tobacco products and fluids such as tea and coffee that one consumes tend to stain one's teeth. These staining and discoloring substances can then permeate the enamel and cause noticeable discoloration of one's teeth. At the same time, some of the food and drinks can cause de-mineralization of the teeth.

One solution to the staining problem is through tooth bleaching. Some dentifrices, like toothpastes, gels, and powders, contain active oxygen or hydrogen peroxide liberating bleaching agents including peroxides, percarbonates and perborates of the alkali and alkaline earth metals or complex compounds containing hydrogen peroxide.

The amount of whitening obtained during tooth bleaching is dependent upon (1) the length of time each day the tray is worn; (2) the number of days the tray is worn; (3) the susceptibility of the teeth to the bleaching agent and (4) the concentration of active peroxides. For maximum whitening, an accelerated treatment time of approximately 18-20 hours per day is recommended.

One concern with some bleaching compositions is that prolonged treatment with highly concentrated bleaching agents present in the composition may contribute to tooth sensitivity following treatment. Even treatments with compositions not known to increase tooth sensitivity in most patients might still cause sensitivity in patients more prone to such sensitivity tendencies.

Another concern is that aggressive brushing, or any treatment with lower pH whitening compositions, as noted in Price et al. (The pH of Tooth-Whitening Products, J Can Dent Assoc, 66:421-6, 2000), may also lead to further de-mineralization of the tooth, decreasing its hardness.

Many attempts have been made to provide dentinal sensitivity relief, sometimes in a separate system from the bleaching system. Other attempts have been made to use a single system to attack both problems. At the same time, attempts have been made to re-mineralize the tooth, again in separate systems.

Therefore, there remains a need for a one-system approach to solving all the above mentioned problems and/or potential problems confronting the tooth.

SUMMARY OF THE INVENTION

The present invention relates to a one-system approach to whitening, sensitivity relief and re-mineralization.

The system may be a 2-component treatment composition having a first component including at least one peroxide compound, at least one source of phosphate and at least one gelling agent; and a second component including at least one source of calcium, strontium and/or mixtures thereof, and at least one gelling agent.

In one embodiment, the system may be a foamable composition.

In another embodiment, the first component may also contain a de-sensitizing agent.

The system also includes a 2-component foamed composition having a first component including at least one peroxide compound, at least one source of phosphate and at least one gelling agent; and a second component including at least one source of calcium, strontium and/or mixtures thereof.

The system further includes a 2-component foamable composition having a first component including at least one peroxide compound, at least one source of phosphate and at least one gelling agent; and a second component including at least one source of calcium, strontium and/or mixtures thereof, and at least one foaming agent.

In one embodiment of the invention, the second component may include at least one source of peroxide.

In another embodiment of the invention, the second component may include a de-sensitizing agent.

In yet another embodiment of the invention, both components may include a de-sensitizing agent.

In a further embodiment of the invention, the first component may also include a gel stabilizer.

In yet a further embodiment of the invention, the first component may be substantially milky, cloudy, opaque or colored, and the second component may be substantially clear, and vice versa; or both components may be substantially milky, cloudy, opaque or colored.

In still another embodiment of the invention, the two-components of the system are adapted to be admixed and applied to the teeth from a dental tray for sustained contact.

In yet still a further embodiment of the invention, the foamable system may form a long lasting, collapsible foam having a half life of at least about 1 hour.

In still yet another embodiment of the invention, the foamed system may be a long lasting, collapsible foam having a half life of at least about a month.

In other embodiments of the invention, the two components of the system may be provided in a two barrel syringe. In one aspect, the syringe may be provided with a dispensing tip. In another aspect, the dispensing tip may be adapted for foaming. In a further aspect, the tip may include a mixer.

In still other embodiment of the invention, the two components of the system may be provided in a container having separate compartments for the components. In one aspect, the container may be provided with a dispensing pump.

The present invention further relates to a system approach for whitening and remineralizing. In one embodiment, the system may include a low peroxide content whitening composition having remineralizing effect. In another embodiment, the system may include a low peroxide content whitening composition having remineralizing effect with sensitivity relief. In yet another embodiment, the system may include a low peroxide content whitening composition having remineralizing effect and fluoride treatment. In a further embodiment, the system may include a low peroxide content whitening composition having remineralizing effect, fluoride treatment and anti-bacterial effect. In others embodiments, any of the combination effects desired may be achieved. In even more embodiments, other agents, including anti-plaque agents, anti-staining agents, vitamin supplements or others that may be beneficial to teeth, breath or even general health care may be included.

The present invention together with the above and other advantages may best be understood from the following detailed description of the exemplary embodiments of the invention.

DETAILED DESCRIPTION OF THE INVENTION

The detailed description set forth below is intended as a description of the presently exemplified dental whitening compositions provided in accordance with aspects of the present invention and is not intended to represent the only forms in which the present invention may be prepared or utilized. The description sets forth the features and the steps for preparing and using the dental whitening compositions of the present invention. It is to be understood, however, that the same or equivalent functions and ingredients incorporated in the dental whitening compositions may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein may be used in the practice or testing of the invention, the exemplified methods, devices and materials are now described.

All publications mentioned herein are incorporated herein by reference for the purposes of describing and disclosing, for example, the compositions and methodologies that are described in the publications which might be used in connection with the presently described invention. The publications listed or discussed above, below and throughout the text are provided solely for their disclosure prior to the filing date of the present application. Nothing herein is to be construed as an admission that the inventors are not entitled to antedate such disclosures by virtue of prior invention.

The bleaching compositions of this invention includes a two-component system, at least one of the components include at least one peroxide compound.

The peroxide containing component may include, for example, metal ion free peroxide compounds. Examples of suitable metal ion free peroxide compounds include hydrogen peroxide and organic peroxides including urea peroxide (carbamide peroxide), glyceryl peroxide, benzoyl peroxide and the like. More for example, peroxides include hydrogen peroxide, carbamide peroxide and mixtures thereof. The total peroxide present in the whitening gel ranges, for example, from about 0.5% by weight to about 45% by weight of the gel, more for example, from about 1% by weight to about 35% by weight of the gel.

When hydrogen peroxide is used, it is usually provided as a 50% aqueous solution. When used alone, the amount of the hydrogen peroxide aqueous solution in the peroxide gel ranges for example, from about 1% to about 60% (0.5% to 30% in the absence of water); more for example, the amount ranges from about 2% to about 40% (1% to 20% in the absence of water).

On the other hand, when carbamide peroxide is used, it is likely to be used in combination with hydrogen peroxide, though it may be used alone.

When used in combination, the carbamide peroxide is generally present, for example, in an amount from about 0% by weight to about 40% by weight, and more for example, in an amount from about 0.5% to about 35% by weight. At the same time, hydrogen peroxide, for example, is provided as a 50% aqueous solution and is generally present in an amount of from about 0.5% to about 30% (0.25% to 15% in the absence of water); more for example, in an amount of about 1% to about 30% (0.5% to 15% in the absence of water).

The peroxide source may be present in either one or both components of the system. When it is also present in the second component, the combined total source of peroxide content is in the same range as is disclosed above.

The composition of the present invention may be an unfoamed, foamed or foamable composition. In general, a foamed composition may include the same or higher peroxide concentration as that present in an unfoamed composition. On the other hand, a foamable composition may include a higher peroxide concentration in the unfoamed state so that the concentration of peroxide after foaming may be the same or higher than the level present in a typical gel. For foamable compositions, the amounts of peroxide noted above may represent those in the foamed state.

For an unfoamed gel system, additional components may be added to form a stable gel. These may include gelling agents, gel stabilizers, humectants, and other adjuvants for improving gel consistency, may be added to one or both components.

Gelling agents which may be used in the preparation of whitening gels include, for example, cellulosic gums, fumed silica, for example, CAB-O-SIL fumed silica provided by Cabot Corporation, and emulsifying waxes such as Polawax (emulsifying wax NF) or Crodafos CES (cetearyl alcohol (and) dicetyl phosphate (and) ceteth-10 phosphate), provided by Croda, Inc., and mixtures thereof, in amounts to provide a stable gel. Some examples of cellulosic gum may include 'Klucel'GF, a hydroxymethyl propylcellulose from Hercules.

In addition to the addition of heat, light and/or chemicals, the amount of whitening obtained during a bleaching process is generally dependent upon (1) the length of time the teeth is in contact with the whitening agent; (2) the number of days the treatment is carried out; (3) the susceptibility of the teeth to the bleaching agent and (4) concentration of active peroxide, as noted above. For maximum whitening, a long treatment time with a highly concentrated bleaching composition is generally recommended, as noted before.

Bleaching activity of a peroxide compound is generally dictated by the availability of active peroxides, and not generally by the actual concentration of peroxide present in the composition. When peroxide is present in solution, active peroxides are readily available. However, a solution, by its nature, is not easily contained, and/or not amenable for sustain action when applied to a patient's teeth, again because it is difficult to confine it to any desired location for any length of time. Thus, a less concentrated peroxide solution requiring longer contact time to be effective is not practical in a solution environment. A more concentrated solution of peroxide, though more efficient in bleaching, is likewise not suitable in a solution environment because it will not solve the confinement and prolonged contact problem. In addition, any concentrated peroxide solution that may come into contact with soft tissue inside a patient's mouth may potentially cause tissue damage. Therefore, to maintain effective bleaching with good containment so as to minimize potential tissue damage, various gelling agents, thickeners, adhesion promoters and/or similar additives may be used, as discussed above in the unfoamed system. These result in the formation of paste, gels, and similar forms, which are effective whitening systems. It is surmised that some of the additives used, though effective in containment and bleaching, may somewhat decrease the bleaching activity by inhibiting the availability of active peroxides, especially if the composition contain thickeners or adhesion promoters derived from polymers of acrylic acid (carbomer), pyrrolidone analog thickeners, or others. Such additives may lead to diminished whitening capacity of peroxides through ionic and covalent interactions within the gel, and act against the desired effect of tooth whitening.

Foaming may be another way to improve substantivity without some of the above mentioned additives. Foamed compositions may also provide prolonged contact without high amounts of additives that may tend to somewhat inhibit the activity of active peroxides, thus further improving the whitening activity. Foams may be formulated with the same or higher amounts of active ingredients and smaller amounts of inactive ingredients. In a given volume, smaller amounts of inactive ingredients such as gelling agents, thickeners, adhesion promoters or similar may be present in the foamed state compared to unfoamed state. Without wishing to be bound to a theory, it is surmised that air performs the function of an inactive ingredient such as a gelling agent, a thickener, an adhesion promoter or mixtures thereof, to give the needed substantivity; but air molecules in general do not inhibit the availability of active peroxides to the same extent as other inactive ingredients needed for substantivity in an unfoamed gel. Thus, a foamed composition has the substantivity of a composition having higher amounts of ingredients such as gelling agents, thickeners, adhesion promoters or similar inactive ingredients, but with more availability of active peroxides for bleaching action even if the same concentration of peroxide is present. In other words, foaming may in effect substitute air bubbles for gelling agents to create substantivity.

Thus, a foamed or foamable composition of the present invention may increase the rate of whitening activity, if desired, without the problems encountered by solutions. Not only is a foamed composition manageable without confinement problems during use, it may also be capable of delivering a high concentration of active peroxide by not inhibiting the availability of active peroxides, and at the same time, may also seek to fill crevices, sometimes seeping into gaps where gaps are not apparent, thus offering effective whitening action not only to the front surface of a tooth, but surfaces in-between teeth as well. Therefore, foaming may potentially provide all the benefits that are not currently available to other whitening systems.

Foams in general also have lower surface tension than their unfoamed counterparts and may therefore be spread as thin as one molecule thick sheets, while at the same time increasing its surface area, thus covering more area with the same volume of whitening composition than their unfoamed counterparts. The ability to lower surface tension may also make the stains easier to remove.

The foamed bubbles, through the forces of capillary action and lowered surface tension, are also themselves good wetting agents, so that a bleaching solution may penetrate through smaller openings, as noted above. The rapid penetration into the tightest spots may also be aided by the distribution of the sizes and shapes of bubbles. Thus, foams may even cause deeper penetration of active peroxide molecules.

It is further surmised that active peroxides may also be captured inside the bubbles of foams. As the bubbles collapse, the active peroxide agent is released to perform whitening actions.

The foamed or foamable composition of the present invention not only has advantages over unfoamed gels, as discussed above, such as flowing between enamel rods, and insuring that more active ingredients get to the areas not previously reachable, but may also provide better sustained action in a home use setting.

For home use, a tray is generally used for sustain contact between the whitening composition and the surface of tooth or teeth to effect whitening. Compositions in the art generally use additives having high adhesion strength to help retain the composition and even the tray in place. Foams may provide such sustain contact without resorting to the use of the kind of adhesion promoting additives used in the art. Foams may also more evenly spread any stress exerted on the teeth or tray. In addition, foamed compositions have lower density and thus are more amenable for sustain contact without gravity drag. Thus, foams not only facilitate the whitening action but may also facilitate the ease of application, penetration into difficult to reach areas, retention and removal. It is further surmised that the active whitening ingredients may be captured inside the bubbles and such bubbles may serve as controlled whitening devices by metering the amount of active peroxides acting on the teeth over time as the bubbles collapse.

In some embodiments, the foamed composition may be made during manufacturing of the gels and may be packaged accordingly. Foam formation may be effected by any agitation or whipping action, use of foaming agents and combinations thereof. Such foams may be made to be long lasting with a desired shelf life, for example, at least about a month.

In other embodiments, foaming agents may be present to render the composition foamable so that foams are generated just prior to use. Some foaming agents may also aid in increasing the adhesion of the gel to a solid surface by allowing it to spread over a greater surface area.

In still other embodiments, foams may be formed just prior to use by agitation with or without any foaming agent.

Thus, some compositions include at least one foaming agent. Different categories of foaming agents are suitable, and they may produce foams in different ways. Suitable foaming agents may include certain surfactants such as anionic, nonionic, amphoteric, zwitterionic, cationic, or mixtures thereof.

Some of these aids in foam formation and some do not. Some surfactants are useful purely for their foaming properties alone, some act only as emulsifiers or wetting agents without foaming, and some even act to reduce foaming. The functions of the surfactants are not necessarily determined by the category they belong to.

Anionic surfactants include, but not limited to water-soluble salts of alkyl sulfates having from about 8 to about 20 carbon atoms in the alkyl radical (such as sodium alkyl sulfate), water-soluble salts of sulfonated monoglycerides of fatty acids having from about 8 to about 20 carbon atoms and mixtures thereof. Examples of anionic surfactants include Sodium lauryl sulfate, sodium coconut monoglyceride sulfonates, phospholipids, sarcosinates, such as sodium lauryl sarcosinate, taurates, sodium lauryl sulfoacetate, sodium lauroyl isethionate, sodium laureth carboxylate, and sodium dodecyl benzenesulfonate. Many of these anionic surfactants are disclosed in U.S. Pat. No. 3,959,458, the content of which is incorporated herein in its entirety by reference.

Nonionic surfactants may include, but not limited, to compounds including a hydrophilic and hydrophobic components (which maybe produced by the condensation of alkylene oxide groups (hydrophilic in nature) with an organic hydrophobic compound which may be aliphatic or alkyl-aromatic in nature). Examples of suitable nonionic surfactants include low viscosity poloxamers (sold under the trade name Pluronic), low viscosity hydroxyethyl cellulose, polysorbates, polyoxyethylene sorbitan esters (sold under the trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures thereof.

Amphoteric surfactants may include, but is not limited to derivatives of aliphatic secondary and tertiary amines in which the aliphatic component may be a straight chain or branched and one of the aliphatic substituents contains from about 8 to about 18 carbon atoms and one contains an anionic water-solubilizing group, such as carboxylate, sulfonate, sulfate, phosphate, phosphonate, betaines, specifically cocamidopropyl betaine, and mixtures thereof.

Many of these nonionic and amphoteric surfactants are disclosed in U.S. Pat. No. 4,051,234, the content of which is incorporated herein by reference in its entirety.

In the present invention, the exemplified surfactants, when used in foamable compositions, are those that not only have some foaming capabilities, but also those with some ability to act as wetting agents.

Actually, any asymmetrical molecule dissolved in water will make at least a weak surfactant. Such weak surfactants may normally not be an effective foaming agent, but its effectiveness may be improved if a foaming dispenser is used. Asymmetrical molecules as used herein include those that include a hydrophilic and a hydrophobic segment, such as some of the nonionic surfactants mentioned above. One end of the molecule is thus polar in nature and dissolves in water, while the other end is nonpolar in nature and avoids water. When in water, the surfactant molecules oriented themselves with their polar ends towards the water molecules, leaving the nonpolar ends free to attract nonpolar molecules. It is surmised that in a foamed or foamable composition of the present invention, the non-polar ends help to lift tooth surface stains, allowing them to be washed away with the water.

The amount of foaming agents may range, for example, from about 0.1% to about 5% by weight of the foamable composition, more for example, from about 0.5% to about 3% by weight, even more for example, less than about 1% by weight.

Still other foaming agents may include reaction products of any base with an acid. These may include, for example, an alkali metal carbonate or bicarbonate, such as sodium bicarbonate, potassium bicarbonate, sodium carbonate or potassium carbonate, or an alkaline metal carbonate or bicarbonate such as magnesium or calcium bicarbonate or carbonate. The amount used may range, for example, from about 1% to about 10% by weight, more for example, from about 3% to about 7%, still more for example, from about 3.5 to about 5.5% by weight of the composition. The amount used may also depend on the volume of foam required. Thus, by varying the amount of foaming agents, the amount of foam produced may be varied accordingly.

Generally, the ratio of acid and base ranges, for example, from about 1:0.5 to 1:25, more for example, from about 1:1 to 1:4, by weight. Suitable acids include strong acids such as water soluble carboxylic acids, phosphoric acids, nitric acids, and/or sulfuric acids.

Additionally, a foaming agent may also be a gaseous material. The gaseous material may be any inert gas or a gas generated by mixing a basic peroxide solution with an acid solution.

Since the whitening activity results when active peroxide comes into contact with the tooth, the foams generated just prior to use may for example, not need to be too long lasting, if the active ingredients are surmised to be captured within the bubbles, but have a substantive body so that the amount of liquid formed, i.e., the collapsing of the foam bubbles to release active peroxide, may be controlled and balanced. Therefore, the exemplary compositions are not only foamable, but are also capable of producing longer lasting, collapsible foams.

The foams generated by a foamable composition generally have half lives of, for example, from about 1 to 10 hours, more for example, from about 2 to 5 hours. A foam having a half life of 2 hours means that 50% of the bubbles would collapse to release the encapsulated whitening agent, or that the volume of the foam is reduced by 50% in about 2 hours after formation, and 75% of all the bubbles are gone, or the volume of the foam is reduced by 75% in about 4 hours.

The collapse time or half lives of the foam depends on a number of factors. For example, the greater the amount of bubbles formed, the longer the collapse time. Also, the lower the viscosity of the thickeners, and/or other inactive ingredients, the shorter the collapse time. The collapse time may also depend on the nature of the other additives to the composition, which have surface active properties e.g., surfactants or preservatives as well as the environment. For example, a drier environment may contribute to faster collapse of bubbles.

For foamed compositions, the collapsible bubbles typically have very extended half lives when confined in the package, for example, at least about a month, more for example, at least about three months. During use, the collapse of the foamed bubbles is aided by the environment, such as the loss of water or solvent to the environment, and the saliva in the patient's mouth. A packaging may be designed so that a foamed composition may have a desired shelf life after the package or container has been opened and the remaining has been exposed to air. A single-use packaging may also be designed.

For example, a lower viscosity gelling agent or thickener may be used. They are not as likely to inhibit the availability of active peroxides to the same extent as a higher viscosity gelling agent. The viscosity is for example, generally less than about 10,000 cps, more for example, less than about 8,000 cps, and even more for example, less than about 5,000 cps.

Suitable foaming agents include foamable surfactants including at least some sodium lauryl Sulfate as the primary foaming agent.

As discussed above, substantivity, i.e. the ability of a product to linger, is a desirable property in any whitening composition. On the other hand when the desired property of a product is the ability to be rinsed off easily, a foaming surfactant would not be used. However, there is a general desire that a whitening composition may both have substantivity and the ease to be rinsed off. When this is desired, foams generated in a "foaming pump", a dispensing tip adapted for foaming, or a dispensing tip including a mixer adapted for foaming may be used. Such foaming devices again may produce foams with desirable properties, while using a minimum of amount of surfactants, for example, less than about 0.5%. At the same time, some combinations of additives may be chosen to produce the desired effect as well, such as by the addition of other foaming agents.

For remineralizing effects, amorphous calcium compounds may be used. Amorphous calcium compounds such as amorphous calcium phosphate (ACP), amorphous calcium phosphate fluoride (ACPF), amorphous calcium carbonate phosphate (ACCP), amorphous calcium carbonate phosphate (ACCP), and amorphous calcium carbonate phosphate fluoride (ACCPF) may be used in remineralizing teeth. These amorphous compounds are disclosed in U.S. Pat. Nos. 5,037,639, 5,268,167, 5,437,857, 5,562,895, 6,000,341, and 6,056,930, the disclosure of each is hereby incorporated by reference in its entirety.

In addition to amorphous calcium compounds, amorphous strontium compounds such as amorphous strontium phosphate (ASP), amorphous strontium phosphate fluoride (ASPF), amorphous strontium calcium phosphate (ASCP), amorphous strontium calcium carbonate phosphate (ASCCP), amorphous strontium carbonate phosphate fluoride (ASCPF) and amorphous strontium calcium carbonate phosphate fluoride (ASCCPF) may be used in re-mineralization, as noted above. These compounds are disclosed in U.S. Pat. No. 5,534,244, the content of which is hereby incorporated by reference in its entirety.

Some of the compounds mentioned above may also be used in fluoridating teeth. All of the above amorphous compounds or solutions which form the amorphous compounds, when applied either onto or into dental tissue, may aid to prevent and/or repair dental weaknesses such as dental caries, exposed roots and dentin sensitivity.

For example, the first component of the whitening system may include a source of phosphate and the second component may include a source of calcium or strontium.

For example, the source of phosphate in the first component may include monosodium phosphate ($NaH_2PO_4$), disodium phosphate, tetrapotassium pyrophosphate or mixtures thereof. As discussed above, the second component may include a source of calcium or strontium, and when the two gel components are mixed, may combine with phosphate to form the various amorphous calcium and/or strontium phosphates.

The source of phosphate may be, for example, present in an amount of from about 0.2% to about 5% by weight, more for example, between about 0.2% to about 4% by weight.

The source of calcium, strontium or combinations thereof in the second component may include, for example, a calcium salt, a strontium salt, or mixtures thereof, more for example, a calcium salt such as calcium nitrate, in an amount of, for example, from about 0.25% by weight to about 1.5% by weight, more for example, about 0.3% to about 1% by weight.

In practice, as much phosphate as possible or practicable may be included. However, amounts of monosodium phosphate in excess of about 4% by weight may tend to affect gel stability.

Surprisingly, the phosphate component present in the first component according to the ranges mentioned above may also act to stabilize the gel. At higher levels, the stabilizing effect gradually disappears.

Additionally, the phosphate salt may further act to adjust the pH of the first component. The pH of the system may be, for example, from about 5 to about 8, more for example, from about 5.5 to about 6.5.

Surprisingly, the amorphous calcium and/or strontium salts present in the composition may also act as sensitivity relief agents. In fact, the present inventors have found that the de-sensitizing effect provided by amorphous calcium phosphate is at least as effective as, if not more effective than, the typical de-sensitizing agents normally used, including some of those discussed below. Therefore, the presence of amorphous calcium and/or strontium salts may potentially replace traditional de-sensitizing agents.

Additional de-sensitizing agents may also be used. Suitable desensitizing agents, if added, may include, for example, alkali nitrates such as potassium nitrate, sodium nitrate and lithium nitrate; and other potassium salts such as potassium chloride and potassium bicarbonate.

The percent of desensitizing agent may be present, for example, up to about 5 percent by weight, more for example, up to about 4 percent by weight, and even more for example, up to about 3 percent by weight.

The de-sensitizing agent may be present in both components of the system and the ranges present above may represent the total in both components. For example, the de-sensitizing agent may be present in approximately equal amounts in each component.

Surprisingly, the de-sensitizing agent also acts to stabilize the gel.

In addition, optional additives including humectants, flavorings, coloring agents, anti-plaque agents, anti-staining compounds, pH adjusting agents, excipients such as emollients, preservatives, other types of stabilizers such as anti-oxidants, chelating agents, tonicity modifiers (such as sodium chloride, mannitol, sorbitol or glucose), spreading agents, and water soluble lubricants, such as propylene glycol, glycerol or polyethylene glycol. The concentration of each may easily be determined by a person skilled in the art. Some of these may be contemplated for a foamed or foamable system.

The humectants contemplated for use in the inventive compositions include water, polyols, such as glycerol, sorbitol, polyethylene glycols, propylene glycols, hydrogenated partially hydrolyzed polysaccharides and the like. A single humectant or a combination is also contemplated. They are generally present in amounts of, for example, up to about 85%, more for example, from about 15% to about 75% of the formulation. For foamable compositions, the amount of humectant present tends more towards the high end of the range.

As mentioned above, lower peroxide content compositions may be contemplated. These low peroxide compositions may be used at home over longer period of time and may be used as a vehicle for the delivery of many other agents that may be beneficial to oral and general health. These compositions may also be used after an in-office whitening treatment to maintain the effect. In addition, a remineralizing composition adapted for prolong use may be beneficial to damaged tooth or teeth, severe caries, or even bone loss.

In one embodiment, the system may include a low peroxide content whitening composition having remineralizing effect. In another embodiment, the system includes a low peroxide content whitening composition having remineralizing effect with sensitivity relief. In yet another embodiment, the system may include a low peroxide content whitening composition having remineralizing effect and fluoride treatment. In a further embodiment, the system may include a low peroxide content whitening composition having remineralizing effect, fluoride treatment and anti-bacterial effect.

In more embodiments, any of the combination effects desired may be achieved. In even more embodiments, other agents, including anti-plaque agents, anti-staining agents, vitamin supplements or others that may be beneficial to teeth, breath or even general health care may be included.

The peroxide content may be in the low end of the range mentioned above, for example, from about 0.5 to about 5%, more for example, from about 0.5 to about 3%. The composition may be foamed or unfoamed.

Though the amorphous calcium and/or strontium salts present in the composition may also act as sensitivity relief agents, additional de-sensitizing agents, such as the potassium salts and similar mentioned above may also be added for additional effect.

Useful fluoridating agents may include metal fluoride salts such as sodium fluoride, sodium monofluorophosphate, potassium fluoride, lithium fluoride, ammonium fluoride, stannous fluoride; zinc ammonium fluoride, tin ammonium fluoride, calcium fluoride and cobalt ammonium fluoride, and water soluble amine hydrofluorides. Generally, sodium fluoride and stannous fluoride.

Some amorphous calcium and strontium salts may also be useful fluoridation agents and include amorphous calcium phosphate fluoride (ACPF), amorphous calcium carbonate phosphate fluoride (ASCPF) (as disclosed in U.S. Pat. Nos. 5,037,639, 5,268,167, 5,437,857, 5,562,895, 6,000,341, and 6,056,930, the disclosure of each is hereby incorporated by reference in its entirety), amorphous strontium phosphate fluoride (ASPF), amorphous strontium carbonate phosphate fluoride (ASCPF) and amorphous strontium calcium carbonate phosphate fluoride (ASCCPF) (as disclosed in U.S. Pat. No. 5,534,244, the content of which is hereby incorporated by reference in its entirety). These compounds may have both remineralizing and fluoridating effects.

Useful antibacterial agents include, for example, phenolics and salicylamides, and sources of certain metal ions such as zinc, copper, silver and stannous ions, for example in salt form such as zinc, copper and stannous chloride, and silver nitrate. These are again present in small quantities when used.

In foamed or foamable form, the advantages of foams mentioned above are also realized in these low peroxide content whitening compositions.

In packaging the tooth whitening composition of the present invention, any convenient way for effecting the separation of the two components before use may be utilized. For example, a single container may be compartmentalized so that the two components are housed in separate compartments and are dispensed simultaneously and admixed prior to application on the teeth. Alternatively, the two components may be housed in separate containers from which the respective components are dispensed for admixture just prior to use. An exemplary packaging is disclosed in U.S. Pat. Nos. 5,819, 988, 6,065,645, 6,394,314, 6,564,972 and 6,698,622, incorporated herein by reference.

In one exemplary embodiment of the present invention, the two components are provided in separate chambers of a dual barrel syringe. In another exemplary embodiment of the invention, the two components of the system are provided in a container having separate compartments for the components.

In any of the packaging methods described, the syringe or the dual-compartment container may be provided with a dispensing tip, or a dispensing tip including a mixer. The mixers may be dynamic or static. Examples of static mixers may include those also disclosed in U.S. Pat. Nos. 5,819,988, 6,065,645, 6,394,314, 6,564,972 and 6,698,622, incorporated herein by reference. Examples of some dynamic mixers may include those disclosed in may include those disclosed in U.S. Pat. Nos. 6,443,61, and 6,457,609; and U.S. Patent Publication No. 2002/0190082; the contents of these are hereby incorporated by reference.

Such dispensing tips or mixers may also be adapted for foaming or the syringe or container is provided with a dispensing pump.

Immediately before use, the two components are mixed together in a 1:2 to a 5:1 ratio (first component to second component) by actuating the syringe or the container. For example, the gels or foams may be mixed in the 1:1 ratio. The admixed whitening gel or foam is applied to the surface of the teeth directly from the syringe or by means of a dental bleaching tray. Other combinations of the components are contemplated by the present invention, depending on the % variation of ingredients present in each component.

Surprisingly, apart from the components for the amorphous compound, such as the source of phosphate and the source of calcium, strontium or mixture, the two components may include approximately the same active ingredients. When the two components of the exemplified embodiment are mixed, the two sources may combine to form calcium phosphate. When applied to the teeth, the calcium phosphate may precipitate onto the surface of the teeth where it may be incorporated into hydroxyapatite, assisting in remineralization of the tooth enamel, as discussed in U.S. Pat. Nos. 5,037, 639, 5,268,167, 5,460,803, 5,534,244, 5,562,895, 6,000,341, and 6,056,930, noted above. The activity of the amorphous calcium and/or strontium compounds is not compromised, even if the source of peroxide and other active ingredients are present in both components. This may result in improved manufacturing efficiency.

In addition, to visibly distinguish the two components, the first component may be made to be substantially milky, cloudy, opaque or colored, while the second component may be made to be substantially clear, or vice versa. In addition, both may be made to be substantially milky, cloudy, opaque or colored, and the distinction is by degree or by color.

Most opacifying agents tend to decrease the stability of peroxide; for example, $TiO_2$ or $ZnO_2$ may cause the decomposition of peroxide, making it less effective for its intended purposes. Surprisingly, $CaCO_3$ is found to be an effective pigment as well as a mixture of mica and $TiO_2$ stabilized with an EDTA salt. Both were found not to affect the peroxide stability, and a white first component resulted. Other opacifying agents having the same effect is also contemplated.

The present invention is further described by the following examples. The ingredients in B were mixed in a Kitchenaide mixer until the hydroxymethyl propylcelluose, available from Hercules Incorporated, Aqualon Division, Hercules Plaza (Wilmington, Del.) and the emulsifying wax were dispersed in the propylene glycol. Then, the ingredients in A were added and mixed together prior to the addition of the ingredients in C. Afterwards, the flavoring and silica in C were added to the thickened dispersion with moderate mixing until dispersed. Finally, if used, Timica Extralarge Sparkle 110S (titanium dioxide/mica, available from Engelhard Corporation, Iselin, N.J.) was added and mixed under vacuum to remove all air/foam. On the other hand, when foamed compositions are made, such foam removal action is not needed, while at the same time, agitation for additional foam production is used. Also, for foamable compositions, foaming agents are added. In either foamed or foamable compositions, a decreased amount of gelling agents, thickeners and/or other inactive ingredients may or may not be present.

First Component, Composition 1

| | | % | Grams | Phase |
|---|---|---|---|---|
| 50% Hydrogen peroxide | 50% water | 3.62 | 10.86 | A |
| TKPP | tetrapotassium pyrophosphate | 0.2 | 0.6 | A |
| Glycerin | | 20 | 60 | A2 |
| carbamide peroxide | urea hygrogen peroxide | 17 | 51 | A2 |
| Antifoaming Agent | silicone emulsion/Dimethyl polysiloxan emulsion/"Dow" | QS | QS | A2 |
| Klucel GF | hydrxypropyl methyl cellulose "Hercules" | 1.981 | 105 | B |
| propylene glycol | "Westco" | 45.733.019 | | |
| Propylene Glycol | "Westco" | 12.68 | 38.04 | B |
| Polawax NF | emulsifying wax NF "Croda" | 6.5 | 19.5 | B |
| Combine A & B in "Kitchenaide" | | | | C |
| Cabosil EH-5 | fumed silica/"Cabot" | 4.5 | 13.5 | C |
| Natural Mint | natural mint flavoring | 0.5 | 1.5 | C |

First Component, Composition 2

| | % | Grams | Phase |
|---|---|---|---|
| Water | 4.62 | 13.86 | A |
| TKPP | 0.2 | 0.6 | A |
| Glycerin | 20 | 60 | A2 |
| carbamide peroxide | 16 | 48 | A2 |
| Antifoaming agent | QS | QS | A2 |
| Klucel GF | 35 | 105 | B |
| Propylene Glycol | 12.68 | 38.04 | B |
| Polawax NF | 6.5 | 19.5 | B |
| Combine A & B in "Kitchenaide" | | | C |
| Cabosil EH-5 | 4.5 | 13.5 | C |
| Mint | 0.5 | 1.5 | C |
| | 100 | | |

First Component, Composition 3

| | % | Grams | Phase |
|---|---|---|---|
| Water | 6.82 | 20.46 | A |
| 50% H$_2$0$_2$ | 5.8 | 17.4 | A |
| TKPP | 0.2 | 0.6 | A |
| Glycerin | 20 | 60 | A2 |
| carbamide peroxide | 8 | 24 | A2 |
| Antifoaming agent | QS | QS | A2 |
| Klucel GF | 35 | 105 | B |
| Propylene Glycol | 12.68 | 38.04 | B |
| Polawax NF | 6.5 | 19.5 | B |
| Combine A & B in "Kitchenaide" | | | C |
| Cabosil EH-5 | 4.5 | 13.5 | C |
| Natural Mint | 0.5 | 1.5 | C |
| | 100 | | |

First Component, Composition 4

| | % | Grams | Phase |
|---|---|---|---|
| Water | 9 | 27 | A |
| 50% H$_2$0$_2$ | 5.8 | 17.4 | A |
| TKPP | 0.2 | 0.6 | A |
| Glycerin | 19 | 57 | A2 |
| carbamide peroxide | 8 | 24 | A2 |
| Antifoaming agent | QS | QS | A2 |
| Klucel GF | 34.5 | 103.5 | B |
| Propylene Glycol | 12 | 36 | B |
| Polawax NF | 6.5 | 19.5 | B |
| Combine A & B in "Kitchenaide" | | | C |
| Cabosil EH-5 | 4.5 | 13.5 | C |
| Natural Mint | 0.5 | 1.5 | C |
| | 100 | | |

First Component, Composition 5

| | % | Grams | Phase |
|---|---|---|---|
| Water | 12.5 | 37.5 | A |
| 50% H$_2$0$_2$ | 4.2 | 12.6 | A |
| TKPP | 0.2 | 0.6 | A |
| glycerin | 16.8 | 50.4 | A2 |
| carbamide peroxide | 6 | 18 | A2 |
| Antifoaming agent | QS | QS | A2 |
| Klucel GF | 37 | 111 | B |
| Propylene Glycol | 11.8 | 35.4 | B |
| Polawax NF | 6.5 | 19.5 | B |
| Combine A & B in "Kitchenaide" | | | C |
| Cabosil EH-5 | 4.5 | 13.5 | C |
| Natural Mint | 0.5 | 1.5 | C |
| | 100 | | |

First Component, Composition 6

| | % | Grams | Phase |
|---|---|---|---|
| Water | 12.5 | 37.5 | A |
| 50% H$_2$0$_2$ | 4.2 | 12.6 | A |
| TKPP | 0.2 | 0.6 | A |
| KNO$_3$ | 2 | 6 | |
| Glycerin | 16.3 | 48.9 | A2 |
| carbamide peroxide | 6 | 18 | A2 |
| Antifoaming agent | QS | QS | A2 |
| Klucel GF | 37 | 111 | B |
| Propylene Glycol | 10.55 | 31.65 | B |
| Polawax NF | 6 | 18 | B |
| Combine A & B in "Kitchenaide" | | | C |
| Timica blend | 0.25 | 0.75 | |
| Cabosil EH-5 | 4.5 | 13.5 | C |
| Natural Mint | 0.5 | 1.5 | C |
| | 100 | 300 | |

First Component, Composition 7

|  | % | Grams | Phase |
|---|---|---|---|
| Water | 12.5 | 37.5 | A |
| 50% $H_2O_2$ | 4.2 | 12.6 | A |
| TKPP | 0.2 | 0.6 | A |
| $KNO_3$ | 2 | 6 | A |
| Glycerin | 16.3 | 48.9 | A2 |
| carbamide peroxide | 6 | 18 | A2 |
| Antifoaming agent | QS | QS | A2 |
| Klucel GF | 37 | 111 | B |
| Propylene Glycol | 10.05 | 30.15 | B |
| Polawax NF | 6 | 18 | B |
| Combine A & B in "Kitchenaide" |  |  | C |
| Timica blend | 0.5 | 1.5 |  |
| $TiO_2$ | 0.25 | 0.75 |  |
| Cabosil EH-5 | 4.5 | 13.5 | C |
| Natural Mint | 0.5 | 1.5 | C |
|  | 100 | 300 |  |

First Component, Composition 8

|  | % | Grams | Phase |
|---|---|---|---|
| Water | 12.5 | 38.1 | A |
| 50% $H_2O_2$ | 4.2 | 12.6 | A |
| TKPP | 0.2 | 0.6 | A |
| Glycerin | 16.8 | 50.4 | A2 |
| carbamide peroxide | 6 | 18 | A2 |
| Antifoaming agent | QS | QS | A2 |
| Klucel GF | 37 | 111 | B |
| Propylene Glycol | 11.8 | 35.4 | B |
| Polawax NF | 6.5 | 19.5 | B |
| Combine A & B in "Kitchenaide" |  |  | C |
| Cabosil EH-5 | 4.5 | 13.5 | C |
| Natural Mint | 0.5 | 1.5 | C |
|  | 100 |  |  |

First Component, Composition 9

|  | % | Grams | Phase |
|---|---|---|---|
| Water | 12.5 | 37.5 | A |
| 50% $H_2O_2$ | 4.2 | 12.6 | A |
| TKPP | 0.2 | 0.6 | A |
| $Na_2HPO_4$ (di-sodium) | 0.5 | 1.5 | A |
| $NaH_2PO_4$ (monosodium) | QS | QS | A |
| $KNO_3$ | 2 | 6 | A |
| Glycerin | 16 | 48 | A2 |
| carbamide peroxide | 6 | 18 | A2 |
| Antifoaming agent | QS | QS | A2 |
| Klucel GF | 37 | 111 | B |
| Propylene Glycol | 9.95 | 29.85 | B |
| Polawax NF | 6 | 18 | B |
| Combine A & B in "Kitchenaide" |  |  | C |
| Timica blend/Titanium Dioxide and Mica/ "Englehard" | 0.5 | 1.5 |  |
| $TiO_2$ | 0.25 | 0.75 |  |
| Cabosil EH-5 | 4.4 | 13.2 | C |
| Natural Mint | 0.5 | 1.5 | C |
|  | 100 | 300 |  |

First Component, Composition 10

|  | % | Grams | Phase |
|---|---|---|---|
| Water | 12.7 | 38.1 | A |
| 50% $H_2O_2$ | 0 | 0 | A |

First Component, Composition 10

|  | % | Grams | Phase |
|---|---|---|---|
| TKPP | 0.2 | 0.6 | A |
| $Na_2HPO_4$ (di-sodium) | 0.5 | 1.5 | A |
| $NaP_2PO_4$ (monosodium) | QS | QS | A |
| $KNO_3$ | 2 | 6 | A |
| Glycerin | 14 | 42 | A2 |
| carbamide peroxide | 12 | 36 | A2 |
| Antifoaming agent | QS | QS | A2 |
| Klucel GF | 37 | 111 | B |
| Propylene Glycol | 9.95 | 29.85 | B |
| Polawax NF | 6 | 18 | B |
| Combine A & B in "Kitchenaide" |  |  | C |
| Timica blend | 0.5 | 1.5 |  |
| $TiO_2$ | 0.25 | 0.75 |  |
| Cabosil EH-5 | 4.4 | 13.2 | C |
| Natural Mint | 0.5 | 1.5 | C |
|  | 100 | 300 |  |

First Component, Composition 11

|  | % | Grams | Phase |
|---|---|---|---|
| Water | 12.5 | 37.5 | A |
| 50% $H_2O_2$ | 4.2 | 12.6 | A |
| TKPP | 0.2 | 0.6 | A |
| $NaH_2PO_4$ (monosodium) | 0.5 | 1.5 | A |
| $Na_2HPO_4$ (di-sodium) | QS | QS | A |
| $KNO_3$ | 2 | 6 | A |
| Glycerin | 16 | 48 | A2 |
| carbamide peroxide | 6 | 18 | A2 |
| Antifoaming agent | QS | QS | A2 |
| Klucel GF | 37 | 111 | B |
| Propylene Glycol | 9.95 | 29.85 | B |
| Polawax NF | 6 | 18 | B |
| Combine A & B in "Kitchenaide" |  |  | C |
| Timica blend | 0.5 | 1.5 |  |
| $TiO_2$ | 0.25 | 0.75 |  |
| Cabosil EH-5 | 4.4 | 13.2 | C |
| Natural Mint | 0.5 | 1.5 | C |
|  | 100 | 300 |  |

First Component, Composition 12

|  | % | Grams | Phase |
|---|---|---|---|
| Water | 8.3 | 24.9 | A |
| 50% $H_2O_2$ | 8.4 | 25.2 | A |
| TKPP | 0.2 | 0.6 | A |
| $KNO_3$ | 2 | 6 |  |
| Glycerin | 16.3 | 48.9 | A2 |
| carbamide peroxide | 6 | 18 | A2 |
| Antifoaming agent | QS | QS | A2 |
| Klucel GF | 37 | 111 | B |
| Propylene Glycol | 10.05 | 30.15 | B |
| Polawax NF | 6 | 18 | B |
| Combine A & B in "Kitchenaide" |  |  | C |
| Timica blend | 0.5 | 1.5 |  |
| $TiO_2$ | 0.25 | 0.75 |  |
| Cabosil EH-5 | 4.5 | 13.5 | C |
| Natural Mint | 0.5 | 1.5 | C |
|  | 100 | 300 |  |

First Component, Composition 13

| | % | Grams | Phase |
|---|---|---|---|
| Water | 12.5 | 37.5 | A |
| 50% $H_2O_2$ | 4.2 | 12.6 | A |
| TKPP | 0.2 | 0.6 | A |
| $KNO_3$ | 2 | 6 | |
| Glycerin | 16.3 | 48.9 | A2 |
| carbamide peroxide | 11.5 | 34.5 | A2 |
| Antifoaming agent | QS | QS | A2 |
| Klucel GF | 37 | 111 | B |
| Propylene Glycol | 10.05 | 30.15 | B |
| Polawax NF | 6 | 18 | B |
| Combine A & B in "Kitchenaide" | | | C |
| Timica blend | 0.5 | 1.5 | |
| $TiO_2$ | 0.25 | 0.75 | |
| Cabosil EH-5 | 4.5 | 13.5 | C |
| Natural Mint | 0.5 | 1.5 | C |
| | 105.5 | 316.5 | |

First Component, Composition 14

| | % | Grams | Phase |
|---|---|---|---|
| Water | 12.3 | 36.9 | A |
| 50% $H_2O_2$ | 4.2 | 12.6 | A |
| TKPP | 0.2 | 0.6 | A |
| $KNO_3$ | 2 | 6 | |
| Glycerin | 11 | 33 | A2 |
| carbamide peroxide | 11.5 | 34.5 | A2 |
| Antifoaming agent | QS | QS | A2 |
| Klucel GF | 37 | 111 | B |
| Propylene Glycol | 10.05 | 30.15 | B |
| Polawax NF | 6 | 18 | B |
| Combine A & B in "Kitchenaide" | | | C |
| Timica blend | 0.5 | 1.5 | |
| $TiO_2$ | 0.25 | 0.75 | |
| Cabosil EH-5 | 4.5 | 13.5 | C |
| Natural Mint | 0.5 | 1.5 | C |
| | 100 | 300 | |

First Component, Composition 15

| | % | Grams | Phase |
|---|---|---|---|
| Water | 9.5 | 28.5 | A |
| 50% $H_2O_2$ | 10.1 | 30.3 | A |
| TKPP | 0.2 | 0.6 | A |
| $KNO_3$ | 2 | 6 | |
| Glycerin | 11.3 | 33.9 | A2 |
| carbamide peroxide | 8.1 | 24.3 | A2 |
| Antifoaming agent | QS | QS | A2 |
| Klucel GF | 37 | 111 | B |
| Propylene Glycol | 10.05 | 30.15 | B |
| Polawax NF | 6 | 18 | B |
| Combine A & B in "Kitchenaide" | | | C |
| Timica blend | 0.5 | 1.5 | |
| $TiO_2$ | 0.25 | 0.75 | |
| Cabosil EH-5 | 4.5 | 13.5 | C |
| Natural Mint | 0.5 | 1.5 | C |
| | 100 | 300 | |

First Component, Composition 16

| | % | Grams | Phase |
|---|---|---|---|
| Water | 12.5 | 37.5 | A |
| 50% $H_2O_2$ | 5.3 | 15.9 | A |

-continued

First Component, Composition 16

| | % | Grams | Phase |
|---|---|---|---|
| TKPP | 0.2 | 0.6 | A |
| $KNO_3$ | 2 | 6 | |
| Glycerin | 9.65 | 28.95 | A2 |
| carbamide peroxide | 14.6 | 43.8 | A2 |
| Antifoaming agent | QS | QS | A2 |
| Klucel GF | 37 | 111 | B |
| Propylene Glycol | 7 | 21 | B |
| Polawax NF | 6 | 18 | B |
| Combine A & B in "Kitchenaide" | | | C |
| Timica blend | 0.5 | 1.5 | |
| $TiO_2$ | 0.25 | 0.75 | |
| Cabosil EH-5 | 4.5 | 13.5 | C |
| Natural Mint | 0.5 | 1.5 | C |
| | 100 | 300 | |

First Component, Composition 17

| | % | Grams | Phase |
|---|---|---|---|
| Water | 5 | 15 | A |
| 50% $H_2O_2$ | 11.8 | 35.4 | A |
| TKPP | 0.2 | 0.6 | A |
| $KNO_3$ | 2 | 6 | |
| Glycerin | 6 | 18 | A2 |
| carbamide peroxide | 16.2 | 48.6 | A2 |
| Antifoaming agent | QS | QS | A2 |
| Klucel GF | 37 | 111 | B |
| Propylene Glycol | 10.05 | 30.15 | B |
| Polawax NF | 6 | 18 | B |
| Combine A & B in Kitchenaide | | | C |
| Timica blend | 0.5 | 1.5 | |
| $TiO_2$ | 0.25 | 0.75 | |
| Cabosil EH-5 | 4.5 | 13.5 | C |
| Natural Mint | 0.5 | 1.5 | C |
| | 100 | 300 | |

First Component, Composition 18

| | % | Grams | Phase |
|---|---|---|---|
| Water | 9.2 | 27.6 | A |
| 50% $H_2O_2$ | 7.7 | 23.1 | A |
| TKPP | 0.2 | 0.6 | A |
| $KNO_3$ | 2 | 6 | A |
| Glycerin | 16.6 | 49.8 | A2 |
| carbamide peroxide | 5.5 | 16.5 | A2 |
| Antifoaming agent | QS | QS | A2 |
| Klucel GF | 37 | 111 | B |
| Propylene Glycol | 10.05 | 30.15 | B |
| Polawax NF | 6 | 18 | B |
| Combine A & B in "Kitchenaide" | | | C |
| Timica blend | 0.5 | 1.5 | C |
| $TiO_2$ | 0.25 | 0.75 | C |
| Cabosil EH-5 | 4.5 | 13.5 | C |
| Natural Mint | 0.5 | 1.5 | C |
| | 100 | 300 | |

First Component, Composition 19

| | % | Grams | Phase |
|---|---|---|---|
| Water | 9.2 | 27.6 | A |
| 50% $H_2O_2$ | 7.7 | 23.1 | A |

First Component, Composition 19

| | % | Grams | Phase |
|---|---|---|---|
| TKPP | 0.2 | 0.6 | A |
| KNO$_3$ | 2 | 6 | A |
| Glycerin | 16.6 | 49.8 | A2 |
| carbamide peroxide | 5.5 | 16.5 | A2 |
| Antifoaming agent | QS | QS | A2 |
| Klucel GF | 37 | 111 | B |
| Propylene Glycol | 10.05 | 30.15 | B |
| Crodaphos | 6 | 18 | B |
| Combine A & B in "Kitchenaide" | | | C |
| Timica blend | 0.5 | 1.5 | C |
| TiO$_2$ | 0.25 | 0.75 | C |
| Cabosil EH-5 | 4.5 | 13.5 | C |
| Natural Mint | 0.5 | 1.5 | C |
| | 100 | 300 | |

First Component, Composition 20

| | % | Grams | Phase |
|---|---|---|---|
| Water | 9.5 | 28.5 | A |
| 50% H$_2$O$_2$ | 10.1 | 30.3 | A |
| TKPP | 0.2 | 0.6 | A |
| KNO$_3$ | 2 | 6 | |
| Glycerin | 11.3 | 33.9 | A2 |
| carbamide peroxide | 8.1 | 24.3 | A2 |
| Antifoaming agent | QS | QS | A2 |
| Klucel GF | 37 | 111 | B |
| Propylene Glycol | 10.05 | 30.15 | B |
| Crodaphos | 6 | 18 | B |
| Combine A & B in "Kitchenaide" | | | C |
| Timica blend | 0.5 | 1.5 | |
| TiO$_2$ | 0.25 | 0.75 | |
| Cabosil EH-5 | 4.5 | 13.5 | C |
| Natural Mint | 0.5 | 1.5 | C |
| | 100 | 300 | |

First Component, Composition 21

| | % | Grams | Phase |
|---|---|---|---|
| Water | 8.3 | 24.9 | A |
| 50% H$_2$O$_2$ | 8.4 | 25.2 | A |
| TKPP | 0.2 | 0.6 | A |
| KNO$_3$ | 2 | 6 | |
| Glycerin | 17.8 | 53.4 | A2 |
| carbamide peroxide | 4.5 | 13.5 | A2 |
| Antifoaming agent | QS | QS | A2 |
| Klucel GF | 37 | 111 | B |
| Propylene Glycol | 10.05 | 30.15 | B |
| Polawax NF | 6 | 18 | B |
| Combine A & B in "Kitchenaide" | | | C |
| Timica blend | 0.5 | 1.5 | |
| TiO$_2$ | 0.25 | 0.75 | |
| Cabosil EH-5 | 4.5 | 13.5 | C |
| Natural Mint | 0.5 | 1.5 | C |
| | 100 | 300 | |

First Component, Composition 22

| | % | Grams | Phase |
|---|---|---|---|
| Water | 8.3 | 24.9 | A |
| 50% H$_2$O$_2$ | 7.3 | 21.9 | A |

First Component, Composition 22

| | % | Grams | Phase |
|---|---|---|---|
| TKPP | 0.2 | 0.6 | A |
| KNO$_3$ | 2 | 6 | A |
| Glycerin | 17.3 | 51.9 | A2 |
| carbamide peroxide | 6.1 | 18.3 | A2 |
| Antifoaming agent | QS | QS | A2 |
| Klucel GF | 37 | 111 | B |
| Propylene Glycol | 10.05 | 30.15 | B |
| Polawax NF | 6 | 18 | B |
| Combine A & B in "Kitchenaide" | | | C |
| Timica blend | 0.5 | 1.5 | |
| TiO$_2$ | 0.25 | 0.75 | |
| Cabosil EH-5 | 4.5 | 13.5 | C |
| Natural Mint | 0.5 | 1.5 | C |
| | 100 | 300 | |

First Component, Composition 23

| | % | Grams | Phase |
|---|---|---|---|
| Water | 8.3 | 24.9 | A |
| 50% H$_2$O$_2$ | 7.3 | 21.9 | A |
| TKPP | 0.2 | 0.6 | A |
| KNO$_3$ | 2 | 6 | |
| Glycerin | 17.3 | 51.9 | A2 |
| carbamide peroxide | 6.1 | 18.3 | A2 |
| Antifoaming agent | QS | QS | A2 |
| Klucel GF | 37 | 111 | B |
| Propylene Glycol | 10.55 | 31.65 | B |
| Polawax NF | 6 | 18 | B |
| Combine A & B in "Kitchenaide" | | | C |
| Timica blend | 0.5 | 1.5 | |
| TiO$_2$ | 0.25 | 0.75 | |
| Cabosil EH-5 | 4.5 | 13.5 | C |
| Natural Mint | 0 | 0 | C |
| | 100 | 300 | |

First Component, Composition 24

| | % | Grams | Phase |
|---|---|---|---|
| Water | 8.3 | 41.5 | A |
| 50% H$_2$O$_2$ | 8.4 | 42 | A |
| TKPP | 0.2 | 1 | A |
| KNO$_3$ | 2 | 10 | |
| Glycerin | 18.3 | 91.5 | A2 |
| carbamide peroxide | 4.5 | 22.5 | A2 |
| Antifoaming agent | QS | QS | A2 |
| Klucel GF | 37 | 185 | B |
| Propylene Glycol | 10.05 | 50.25 | B |
| Polawax NF | 6 | 30 | B |
| Combine A & B in "Kitchenaide" | | 0 | C |
| Timica blend | 0.5 | 2.5 | |
| TiO$_2$ | 0.25 | 1.25 | |
| Cabosil EH-5 | 4.5 | 22.5 | C |
| Natural Mint | 0 | 0 | C |
| | 100 | 500 | |

First Component, Composition 25

| | % | Grams | Phase |
|---|---|---|---|
| Water | 12.5 | 37.5 | A |
| 50% H$_2$O$_2$ | 3.3 | 9.9 | A |

First Component, Composition 25

| | % | Grams | Phase |
|---|---|---|---|
| TKPP | 0.2 | 0.6 | A |
| KNO$_3$ | 2 | 6 | A |
| Glycerin | 17.7 | 53.1 | A2 |
| carbamide peroxide | 5.5 | 16.5 | A2 |
| Antifoaming agent | QS | QS | A2 |
| Klucel GF | 37 | 111 | B |
| Propylene Glycol | 10.05 | 30.15 | B |
| Polawax NF | 6 | 18 | B |
| Combine A & B in "Kitchenaide" | | | C |
| Timica blend | 0.5 | 1.5 | |
| TiO$_2$ | 0.25 | 0.75 | |
| Cabosil EH-5 | 4.5 | 13.5 | C |
| Natural Mint | 0.5 | 1.5 | C |
| | 100 | 300 | |

First Component, Composition 26

| | % | Grams | Phase |
|---|---|---|---|
| Water | 12.5 | 37.5 | A |
| 50% H$_2$O$_2$ | 3.3 | 9.9 | A |
| TKPP | 0.2 | 0.6 | A |
| KNO$_3$ | 0 | 0 | |
| Glycerin | 18.7 | 56.1 | A2 |
| carbamide peroxide | 5.5 | 16.5 | A2 |
| Antifoaming agent | QS | QS | A2 |
| Klucel GF | 38 | 114 | B |
| Propylene Glycol | 10.05 | 30.15 | B |
| Polawax NF | 6 | 18 | B |
| Combine A & B in "Kitchenaide" | | | C |
| Timica blend | 0.5 | 1.5 | |
| TiO$_2$ | 0.25 | 0.75 | |
| Cabosil EH-5 | 4.5 | 13.5 | C |
| Natural Mint | 0.5 | 1.5 | C |
| | 100 | 300 | |

First Component, Composition 27

| | % | Grams | Phase |
|---|---|---|---|
| Water | 8.3 | 24.9 | A |
| 50% H$_2$O$_2$ | 8.4 | 25.2 | A |
| TKPP | 0.2 | 0.6 | A |
| KNO$_3$ | 0 | 0 | |
| Glycerin | 18.8 | 56.4 | A2 |
| carbamide peroxide | 4.5 | 13.5 | A2 |
| Antifoaming agent | QS | QS | A2 |
| Klucel GF | 38 | 114 | B |
| Propylene Glycol | 10.05 | 30.15 | B |
| Polawax NF | 6 | 18 | B |
| Combine A & B in "Kitchenaide" | | | C |
| Timica blend | 0.5 | 1.5 | |
| TiO$_2$ | 0.25 | 0.75 | |
| Cabosil EH-5 | 4.5 | 13.5 | C |
| Natural Mint | 0.5 | 1.5 | C |
| | 100 | 300 | |

First Component, Composition 28

| | % | Grams | Phase |
|---|---|---|---|
| Water | 9.5 | 28.5 | A |
| 50% H$_2$O$_2$ | 10.1 | 30.3 | A |
| TKPP | 0.2 | 0.6 | A |
| KNO$_3$ | 0 | 0 | |
| Glycerin | 12.3 | 36.9 | A2 |
| carbamide peroxide | 8.1 | 24.3 | A2 |
| Antifoaming agent | QS | QS | A2 |
| Klucel GF | 38 | 114 | B |
| Propylene Glycol | 10.05 | 30.15 | B |
| Polawax NF | 6 | 18 | B |
| Combine A & B in "Kitchenaide" | | | C |
| Timica blend | 0.5 | 1.5 | |
| TiO$_2$ | 0.25 | 0.75 | |
| Cabosil EH-5 | 4.5 | 13.5 | C |
| Natural Mint | 0.5 | 1.5 | C |
| | 100 | 300 | |

First Component, Composition 29

| | % | Grams | Phase |
|---|---|---|---|
| Water | 8.3 | 12.45 | A |
| 50% H$_2$O$_2$ | 8.4 | 12.6 | A |
| TKPP | 0.2 | 0.3 | A |
| EDTA | 0.5 | 0.75 | |
| KNO$_3$ | 2 | 3 | |
| Glycerin | 17.55 | 26.325 | A2 |
| carbamide peroxide | 4.5 | 6.75 | A2 |
| Antifoaming agent | QS | QS | A2 |
| Klucel GF | 37 | 55.5 | B |
| Propylene Glycol | 10.05 | 15.075 | B |
| Polawax NF | 6 | 9 | B |
| Combine A & B in "Kitchenaide" | | | C |
| Timica blend | 0.5 | 0.75 | |
| TiO$_2$ | 0 | 0 | |
| Cabosil EH-5 | 4.5 | 6.75 | C |
| Natural Mint | 0.5 | 0.75 | C |
| | 100 | 150 | |

To summarize, the range of ingredients in the first component in the above examples are as follows:

a 50% hydrogen peroxide solution is, for example, from about 2% to about 15%, more for example, from about 4% to about 12%; carbamide peroxide is, for example, from about 3% to about 20%, more for example, from about 4% to about 17.0%; aerosol, such as Cabosil EH-5, is, for example, from about 2% to about 5%, more for example, about 4.5%; glycerin is, for example, from about 5% to about 25%, more for example, from about 6% to about 20.0%; gelling agent such as Klucel GF is, for example, from about 1% to about 40%, more for example, from about 2% to about 38%, Polawax NF is, for example, from about 5% to about 10%, more for example, from about 5% to about 7%; propylene glycol is, for example, from about 5% to about 15%, more for example, from about 7% to about 13%, and timica blend/titanium dioxide and mica/"Englehard" is, for example, from about 0.2% to about 1%, more for example, from about 0.25% to about 0.75%. Other ranges may be used without detracting from the present invention.

Second Component, Composition 1

| | % | Grams | Phase |
|---|---|---|---|
| Water | 9.35 | 28.05 | A |
| 50% H$_2$O$_2$ | 8 | 24 | A |

Second Component, Composition 1

|  | % | Grams | Phase |
|---|---|---|---|
| 10% KOH | QS | QS | A |
| Ca(NO$_3$)$_2$ | 0.5 | 1.5 | A |
| KNO$_3$ | 0 | 0 | A |
| Glycerin | 21 | 63 | A2 |
| carbamide peroxide | 5.1 | 15.3 | A2 |
| Antifoaming Agent | QS | QS | A2 |
| Klucel GF | 40 | 120 | B |
| Propylene Glycol | 8.3 | 24.9 | B |
| Polawax NF | 1.25 | 3.75 | B |
| Combine A & B in ":Kitchenaide" |  |  | C |
| Cabosil EH-5 | 6 | 18 | C |
| Natural Mint | 0.5 | 1.5 | C |
|  | 100 | 300 |  |

Second Component, Composition 2

|  | % | Grams | Phase |
|---|---|---|---|
| Water | 4.72 | 14.46 | A |
| 10% KOH | QS | QS | A |
| Ca(NO$_3$)$_2$ | 0.5 | 1.5 | A |
| Glycerin | 20 | 60 | A2 |
| carbamide peroxide | 16 | 48 | A2 |
| Antifoaming Agent | QS | QS | A2 |
| Klucel GF | 35 | 105 | B |
| Propylene Glycol | 12.18 | 36.54 | B |
| Polawax NF | 6.5 | 19.5 | B |
| Combine A & B in "Kitchenaide" |  |  | C |
| Cabosil EH-5 | 4.5 | 13.5 | C |
| Natural Mint | 0.5 | 1.5 | C |
|  | 100 | 300 |  |

Second Component, Composition 3

|  | % | Grams | Phase |
|---|---|---|---|
| Water | 7.02 | 21.06 | A |
| 50% H$_2$O$_2$ | 5.8 | 17.4 | A |
| 10% KOH | QS | QS | A |
| Ca(NO$_3$)$_2$ | 0.5 | 1.5 | A |
| Glycerin | 20 | 60 | A2 |
| carbamide peroxide | 8 | 24 | A2 |
| Antifoaming Agent | QS | QS | A2 |
| Klucel GF | 35 | 105 | B |
| Propylene Glycol | 12.18 | 36.54 | B |
| Polawax NF | 6.5 | 19.5 | B |
| Combine A & B in "Kitchenaide" |  |  | C |
| Cabosil EH-5 | 4.5 | 13.5 | C |
| Natural Mint | 0.5 | 1.5 | C |
|  | 100 | 300 |  |

Second Component, Composition 4

|  | % | Grams | Phase |
|---|---|---|---|
| Water | 9 | 27 | A |
| 50% H$_2$O$_2$ | 5.8 | 17.4 | A |
| 10% KOH | QS | QS | A |
| Ca(NO$_3$)$_2$ | 0.5 | 1.5 | A |
| Glycerin | 18.7 | 56.1 | A2 |
| carbamide peroxide | 8 | 24 | A2 |
| Antifoaming agent | QS | QS | A2 |
| Klucel GF | 34.5 | 103.5 | B |
| Propylone Glycol | 12 | 36 | B |
| Polawax NF | 6.5 | 19.5 | B |
| Combine A & B in "Kitchenaide" |  |  | C |
| Cabosil EH-5 | 4.5 | 13.5 | C |
| Natural Mint | 0.5 | 1.5 | C |
|  | 100 | 300 |  |

Second Component, Composition 5

|  | % | Grams | Phase |
|---|---|---|---|
| Water | 12.5 | 37.5 | A |
| 50% H$_2$O$_2$ | 4.2 | 12.6 | A |
| 10% KOH | QS | QS | A |
| Ca(NO$_3$)$_2$ | 0.5 | 1.5 | A |
| Glycerin | 16.5 | 49.5 | A2 |
| carbamide peroxide | 6 | 18 | A2 |
| Antifoaming agent | QS | QS | A2 |
| Klucel GF | 37 | 111 | B |
| Propylene Glycol | 11.8 | 35.4 | B |
| Polawax NF | 6.5 | 19.5 | B |
| Combine A & B in "Kitchenaide" |  |  | C |
| Cabosil EH-5 | 4.5 | 13.5 | C |
| Natural Mint | 0.5 | 1.5 | C |
|  | 100 | 300 |  |

Second Component, Composition 6

|  | % | Grams | Phase |
|---|---|---|---|
| Water | 12.5 | 37.5 | A |
| 50% H$_2$O$_2$ | 4.2 | 12.6 | A |
| 10% KOH | QS | QS | A |
| Ca(NO$_3$)$_2$ | 0.5 | 1.5 | A |
| Glycerin | 17 | 51 | A2 |
| carbamide peroxide | 6 | 18 | A2 |
| Antifoaming agent | QS | QS | A2 |
| Klucel GF | 41 | 123 | B |
| Propylene Glycol | 12.3 | 36.9 | B |
| Combine A & B in "Kitchenaide" |  |  | C |
| Cabosil EH-5 | 6 | 18 | C |
| Natural Mint | 0.5 | 1.5 | C |
|  | 100 | 300 |  |

Second Component, Composition 7

|  | % | Grams | Phase |
|---|---|---|---|
| Water | 13.5 | 40.5 | A |
| 50% H$_2$O$_2$ | 4.2 | 12.6 | A |
| 10% KOH | QS | QS | A |
| Ca(NO$_3$)$_2$ | 0.5 | 1.5 | A |
| KNO$_3$ | 2 | 6 | A |
| Glycerin | 14.5 | 43.5 | A2 |
| carbamide peroxide | 6 | 18 | A2 |
| Antifoaming agent | QS | QS | A2 |
| Klucel GF | 41 | 123 | B |
| Propylene Glycol | 11.8 | 35.4 | B |
| Combine A & B in "Kitchenaide" |  |  | C |

| Second Component, Composition 7 | | | |
|---|---|---|---|
| | % | Grams | Phase |
| Cabosil EH-5 | 6 | 18 | C |
| Natural Mint | 0.5 | 1.5 | C |
| | 100 | 300 | |

| Second Component, Composition 8 | | | |
|---|---|---|---|
| | % | Grams | Phase |
| Water | 12.5 | 37.5 | A |
| 50% $H_2O_2$ | 4.2 | 12.6 | A |
| 10% KOH | QS | QS | A |
| $Ca(NO_3)_2$ | 0.5 | 1.5 | A |
| $KNO_3$ | 2 | 6 | A |
| Glycerin | 15 | 45 | A2 |
| carbamide peroxide | 6 | 18 | A2 |
| Antifoaming agent | QS | QS | A2 |
| Klucel GF | 39 | 117 | B |
| Propylene Glycol | 12.3 | 36.9 | B |
| Polawax NF | 2 | 6 | B |
| Combine A & B in "Kitchenaide" | | | C |
| Cabosil EH-5 | 6 | 18 | C |
| Natural Mint | 0.5 | 1.5 | C |
| | 100 | 300 | |

| Second Component, Composition 9 | | | |
|---|---|---|---|
| | % | Grams | Phase |
| Water | 13.25 | 39.75 | A |
| 50% $H_2O_2$ | 4.2 | 12.6 | A |
| 10% KOH | QS | QS | A |
| $Ca(NO_3)_2$ | 0.5 | 1.5 | A |
| $KNO_3$ | 2 | 6 | A |
| Glycerin | 19 | 57 | A2 |
| carbamide peroxide | 6 | 18 | A2 |
| Antifoaming agent | QS | QS | A2 |
| Klucel GF | 39 | 117 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

| Second Component, Composition 10 | | | |
|---|---|---|---|
| | % | Grams | Phase |
| Water | 13.75 | 41.25 | A |
| 50% $H_2O_2$ | 4.2 | 12.6 | A |
| 10% KOH | QS | QS | A |
| $KNO_3$ | 2 | 6 | A |
| Glycerin | 19 | 57 | A2 |
| carbamide peroxide | 6 | 18 | A2 |
| Antifoaming agent | QS | QS | A2 |
| Klucel GF | 39 | 117 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

| Second Component, Composition 11 | | | |
|---|---|---|---|
| | % | Grams | Phase |
| Water | 13.45 | 40.35 | A |
| 50% $H_2O_2$ | 4.2 | 12.6 | A |
| 10% KOH | QS | QS | A |
| $Ca(NO_3)_2$ | 0.5 | 1.5 | A |
| Na Edatate | 0.3 | 0.9 | A |
| $KNO_3$ | 2 | 6 | A |
| Glycerin | 18.5 | 55.5 | A2 |
| carbamide peroxide | 6 | 18 | A2 |
| Antifoaming agent | QS | QS | A2 |
| Klucel GF | 39 | 117 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

| Second Component, Composition 12 | | | |
|---|---|---|---|
| | % | Grams | Phase |
| Water | 12.95 | 38.85 | A |
| 50% $H_2O_2$ | 4.2 | 12.6 | A |
| 10% KOH | QS | QS | A |
| $Ca(NO_3)_2$ | 0.5 | 1.5 | A |
| Na Edatate | 0.3 | 0.9 | A |
| $KNO_3$ | 2 | 6 | A |
| Glycerin | 19 | 57 | A2 |
| carbamide peroxide | 6 | 18 | A2 |
| Antifoaming agent | QS | QS | A2 |
| Klucel GF | 39 | 117 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

| Second Component, Composition 13 | | | |
|---|---|---|---|
| | % | Grams | Phase |
| Water | 13.25 | 39.75 | A |
| 50% $H_2O_2$ | 4.2 | 12.6 | A |
| 10% KOH | QS | QS | A |
| $Ca(NO_3)_2$ | 0.5 | 1.5 | A |
| $KNO_2$ | 2 | 6 | A |
| Glycerin | 19 | 57 | A2 |
| carbamide peroxide | 6 | 18 | A2 |
| Antifoaming agent | QS | QS | A2 |
| Klucel GF | 39 | 117 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| 50% KOH | QS | QS | C |
| | 100 | 300 | |

Second Component, Composition 14

| | % | Grams | Phase |
|---|---|---|---|
| Water | 15.05 | 45.15 | A |
| 50% $H_2O_2$ | 8.4 | 25.2 | A |
| 10% KOH | QS | QS | A |
| $Ca(NO_3)_2$ | 0.5 | 1.5 | A |
| $KNO_3$ | 2 | 6 | A |
| Glycerin | 19 | 57 | A2 |
| carbamide peroxide | 0 | 0 | A2 |
| Antifoaming agent | QS | QS | A2 |
| Klucel GF | 39 | 117 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| 50% KOH | QS | QS | C |
| | 100 | 300 | |

Second Component, Composition 15

| | % | Grams | Phase |
|---|---|---|---|
| Water | 10.25 | 30.75 | A |
| 50% $H_2O_2$ | 10.1 | 30.3 | A |
| 10% KOH | QS | | A |
| $Ca(NO_3)_2$ | 0.5 | 1.5 | |
| $KNO_3$ | 2 | 6 | |
| Glycerin | 14 | 42 | A2 |
| carbamide peroxide | 8.1 | 24.3 | A2 |
| Antifoaming agent | QS | QS | A2 |
| Klucel GF | 39 | 117 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

Second Component, Composition 16

| | % | Grams | Phase |
|---|---|---|---|
| Water | 10.25 | 30.75 | A |
| 50% $H_2O_2$ | 10.1 | 30.3 | A |
| 10% KOH | QS | | A |
| $Ca(NO_3)_2$ | 0.5 | 1.5 | |
| $KNO_3$ | 2 | 6 | |
| Glycerin | 14 | 42 | A2 |
| carbamide peroxide | 8.1 | 24.3 | A2 |
| Antifoaming agent | QS | QS | A2 |
| Klucel GF | 39 | 117 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

Second Component, Composition 17

| | % | Grams | Phase |
|---|---|---|---|
| Water | 13.75 | 41.25 | A |
| 50% $H_2O_2$ | 3.6 | 10.8 | A |
| 10% KOH | QS | QS | A |
| $Ca(NO_3)_2$ | 0.5 | 1.5 | A |
| $KNO_3$ | 2 | 6 | A |
| Glycerin | 20 | 60 | A2 |
| carbamide peroxide | 5.1 | 15.3 | A2 |
| Antifoaming agent | QS | QS | A2 |
| Klucel GF | 39 | 117 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

Second Component, Composition 18

| | % | Grams | Phase |
|---|---|---|---|
| Water | 13.5 | 40.5 | A |
| 50% $H_2O_2$ | 3.85 | 11.55 | A |
| 10% KOH | QS | QS | A |
| $Ca(NO_3)_2$ | 0.5 | 1.5 | A |
| $KNO_3$ | 2 | 6 | A |
| Glycerin | 19.6 | 58.8 | A2 |
| carbamide peroxide | 5.5 | 16.5 | A2 |
| Antifoaming agent | QS | QS | A2 |
| Klucel GF | 39 | 117 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

Second Component, Composition 19

| | % | Grams | Phase |
|---|---|---|---|
| Water | 10.25 | 30.75 | A |
| 50% $H_2O_2$ | 5.3 | 15.9 | A |
| 10% KOH | QS | | A |
| $Ca(NO_3)_2$ | 0.5 | 1.5 | |
| $KNO_3$ | 2 | 6 | |
| Glycerin | 12.3 | 36.9 | A2 |
| carbamide peroxide | 14.6 | 43.8 | A2 |
| Antifoaming agent | QS | QS | A2 |
| Klucel GF | 39 | 117 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

Second Component, Composition 20

| | % | Grams | Phase |
|---|---|---|---|
| Water | 5 | 15 | A |
| 50% $H_2O_2$ | 11.8 | 35.4 | A |
| 10% KOH | QS | | A |
| $Ca(NO_3)_2$ | 0.5 | 1.5 | |
| $KNO_3$ | 2 | 6 | |
| Glycerin | 9.45 | 28.35 | A2 |

-continued

| Second Component, Composition 20 | | | |
|---|---|---|---|
| | % | Grams | Phase |
| carbamide peroxide | 16.2 | 48.6 | A2 |
| Antifoaming agent | QS | QS | A2 |
| Klucel GF | 39 | 117 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

| Second Component, Composition 21 | | | |
|---|---|---|---|
| | % | Grams | Phase |
| Water | 13.5 | 40.5 | A |
| 50% H$_2$O$_2$ | 3.85 | 11.55 | A |
| 10% KOH | QS | QS | A |
| Ca(NO$_3$)$_2$ | 0.5 | 1.5 | A |
| KNO$_3$ | 2 | 6 | A |
| Glycerin | 19.6 | 58.8 | A2 |
| carbamide peroxide | 5.5 | 16.5 | A2 |
| Antifoaming agent | QS | QS | A2 |
| Klucel GF | 39 | 117 | B |
| Propylene Glycol | 8.3 | 24.9 | B |
| Crodaphos | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

| Second Component, Composition 22 | | | |
|---|---|---|---|
| | % | Grams | Phase |
| Water | 10.25 | 30.75 | A |
| 50% H$_2$O$_2$ | 10.1 | 30.3 | A |
| 10% KOH | QS | | A |
| Ca(NO$_3$)$_2$ | 0.5 | 1.5 | |
| KNO$_3$ | 2 | 6 | |
| Glycerin | 14 | 42 | A2 |
| carbamide peroxide | 8.1 | 24.3 | A2 |
| Antifoaming agent | QS | QS | A2 |
| Klucel GF | 39 | 117 | B |
| Propylene Glycol | 8.3 | 24.9 | B |
| Crodaphos | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

| Second Component, Composition 23 | | | |
|---|---|---|---|
| | % | Grams | Phase |
| Water | 13.25 | 39.75 | A |
| 50% H$_2$O$_2$ | 3.3 | 9.9 | A |
| 10% KOH | QS | QS | A |
| Ca(NO$_3$)$_2$ | 0.5 | 1.5 | A |
| KNO$_3$ | 2 | 6 | A |
| Glycerin | 20.4 | 61.2 | A2 |
| carbamide peroxide | 5.5 | 16.5 | A2 |
| Antifoaming agent | QS | QS | A2 |
| Klucel GF | 39 | 117 | B |

-continued

| Second Component, Composition 23 | | | |
|---|---|---|---|
| | % | Grams | Phase |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

| Second Component, Composition 24 | | | |
|---|---|---|---|
| | % | Grams | Phase |
| Water | 13.25 | 39.75 | A |
| 50% H$_2$O$_2$ | 3.3 | 9.9 | A |
| 10% KOH | QS | QS | A |
| Ca(NO$_3$)$_2$ | 0.5 | 1.5 | A |
| KNO$_3$ | 0 | 0 | A |
| Glycerin | 21.4 | 64.2 | A2 |
| carbamide peroxide | 5.5 | 16.5 | A2 |
| Antifoaming agent | QS | QS | A2 |
| Klucel GF | 40 | 120 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

| Second Component, Composition 25 | | | |
|---|---|---|---|
| | % | Grams | Phase |
| Water | 13.75 | 41.25 | A |
| 50% H$_2$O$_2$ | 3.6 | 10.8 | A |
| 10% KOH | QS | QS | A |
| Ca(NO$_3$)$_2$ | 0.5 | 1.5 | A |
| KNO$_3$ | 0 | 0 | A |
| Glycerin | 21 | 63 | A2 |
| carbamide peroxide | 5.1 | 15.3 | A2 |
| Antifoaming agent | QS | QS | A2 |
| Klucel GF | 40 | 120 | B |
| Propylene Glycol | 8.3 | 24.9 | B |
| Polawax NF | 1.25 | 3.75 | B |
| Combine A & B in "Kitchenaide" | | | C |
| Cabosil EH-5 | 6 | 18 | C |
| Natural Mint | 0.5 | 1.5 | C |
| | 100 | 300 | |

| Second Component, Composition 26 | | | |
|---|---|---|---|
| | % | Grams | Phase |
| Water | 10.25 | 30.75 | A |
| 50% H$_2$O$_2$ | 10.1 | 30.3 | A |
| 10% KOH | QS | | A |
| Ca(NO$_3$)$_2$ | 0.5 | 1.5 | |
| KNO$_3$ | 0 | 0 | |
| Glycerin | 15 | 45 | A2 |
| carbamide peroxide | 8.1 | 24.3 | A2 |
| Antifoaming agent | QS | QS | A2 |
| Klucel GF | 40 | 120 | B |
| Propylene Glycol | 8.3 | 24.9 | B |
| Polawax NF | 1.25 | 3.75 | B |
| Combine A & B in "Kitchenaide" | | | C |

Second Component, Composition 26

|  | % | Grams | Phase |
|---|---|---|---|
| Cabosil EH-5 | 6 | 18 | C |
| Natural Mint | 0.5 | 1.5 | C |
|  | 100 | 300 |  |

Second Component, Composition 27

|  | % | Grams | Phase |
|---|---|---|---|
| 50% Hydrogen peroxide | 3.62 | 10.86 | A |
| 50% KOH | QS | QS | A |
| CaCO$_3$ | 0.2 | 0.6 | A |
| Glycerin | 20 | 60 | A2 |
| carbamide peroxide | 17 | 51 | A2 |
| Antifoaming agent | QS | QS | A2 |
| Klucel GF | 35 | 105 | B |
| Propylene Glycol | 12.68 | 38.04 | B |
| Polawax NF | 6.5 | 19.5 | B |
| Combine A & B in "Kitchenaide" |  |  | C |
| Cabosil EH-5 | 4.5 | 13.5 | C |
| Natural Mint | 0.5 | 1.5 | C |
|  | 100 | 300 |  |

To summarize, the range of ingredients in the second component in the above examples are as follows:

a 50% hydrogen peroxide solution is, for example, from about 2% to about 15%, more for example, from about 4% to about 12%; carbamide peroxide is, for example, from about 3% to about 15%, more for example, from about 5% to about 12.0%; aerosol, such as Cabosil EH-5, is, for example, from about 2% to about 10%, more for example, about 4% to about 6%, and lower ranges are present for foamable or foamed compositions; glycerin is, for example, from about 5% to about 25%, more for example, from about 9% to about 22%; gelling agent such as Klucel GF is, for example, from about 25% to about 50%, more for example, from about 30% to about 45%, Polawax NF is, for example, from about 1% to about 10%, more for example, from about 1% to about 7%; and propylene glycol is, for example, from about 5% to about 15%, more for example, from about 7% to about 13%. Other ranges may be sued without detracting from the present invention.

The foam made with any of the above compositions are very long lasting, for example, more than 8 hours, when the amounts of gelling agents and similar ingredients remained the same as shown in the above examples. For some of the compositions of the second component, the foam formed was not as stiff as the foam formed with some of the first component compositions due to the lower viscosities of these second components.

Having described the invention with reference to accompanying illustrations and examples of the invention, it is contemplated that other changes can be made without departing from the spirit or scope of the invention as set forth in the appended claims.

The invention claimed is:

1. A method of whitening teeth comprising of the acts of:
mixing a two-component whitening composition just prior to use, wherein said two-component whitening composition comprises: (i) a first component comprising at least one peroxide compound, at least one source of phosphate, and at least one gelling agent; and (ii) a second component comprising at least one source of calcium, strontium or a mixture thereof, and the at least one gelling agent; wherein said source of calcium, strontium or combinations thereof in the second component comprises an amount of from about 0.25% by weight to about 1.5% by weight of the second component; and
applying said whitening composition to at least one tooth for sustained contact;
wherein only when the first component and second component are combined, said source of phosphate in said first component combines with the source of calcium, strontium or combinations thereof in said second component to form amorphous calcium and/or amorphous strontium phosphates in situ to re-mineralize the teeth.

2. The teeth whitening method of claim 1 wherein said second component comprises at least one peroxide compound.

3. The teeth whitening method of claim 1 wherein said second component further comprises an ingredient selected from a group consisting of a de-sensitizing agent, an antibacterial agent, a fluoridating agent, a vitamin supplement, an anti-staining agent, an anti-plaque agent and mixtures thereof.

4. The teeth whitening method of claim 1 wherein the first component is visually distinguishable from the second component.

5. The teeth whitening method of claim 1 further comprising the act of dispensing said mixed whitening composition into a dental tray and placing said dental try onto the teeth for sustained contact.

6. The teeth whitening method of claim 1 wherein said peroxide present in said whitening composition ranges from about 0.5% by weight to about 45% by weight of said whitening composition.

7. The teeth whitening method of claim 1 wherein said peroxide present in the whitening composition ranges from about 1% by weight to about 35% by weight of said whitening composition.

8. The teeth whitening method of claim 1 wherein said source of phosphate in the first component is selected from the group consisting of monosodium phosphate (NaH$_2$PO$_4$), disodium phosphate, tetrapotassium pyrophosphate and mixtures thereof.

9. The teeth whitening method of claim 1 wherein said source of phosphate in said first component is present in an amount of from about 0.2% to about 5% by weight of said first component.

10. The teeth whitening method of claim 1 wherein said source of calcium or strontium, or combinations thereof in said second component comprises a calcium salt, a strontium salt, or mixtures thereof.

11. The teeth whitening method of claim 1 wherein said source of calcium in the second component comprises calcium nitrate.

12. The teeth whitening method of claim 3 wherein said de-sensitizing agent comprises potassium nitrate.

13. The teeth whitening method of claim 12 wherein potassium nitrate is present up to about 5% by weight of said whitening composition.

14. The teeth whitening method of claim 1 further comprising a de-sensitizing agent in said first component.

15. The method of claim 1, wherein said two-components are packaged in a dual-barrel syringe.

16. The method of claim 1, wherein said at least one peroxide compound includes a mixture of hydrogen peroxide and carbamide peroxide.

17. The method of claim 1, wherein the at least one gelling agent includes a mixture of propylene glycol, a blend of titanium dioxide and mica, cellulosic gums, fumed silica, and emulsifying waxes including cetearyl alcohol and dicetyl phosphate and ceteth-10 phosphate.

18. The method of claim 3, wherein the antibacterial agent includes a mixture of phenolics, salicylamides, and sources of metal ions.

19. The method of claim 1, further comprising the act of forming the at least one peroxide compound inside bubbles to provide desired amount of the at least one peroxide compound on the teeth over time as the bubbles collapse.

20. The method of claim 1, wherein one of the first component and the second component is colored and another the first component and the second component is clear.

21. The method of claim 1, wherein the first component and the second component have a color, and the first component and the second component are visibly different having a different degree of the color.

22. The method of claim 1, wherein one of the first component and the second component includes a pigment comprising $CaCO_3$.

23. The method of claim 1, wherein the at least one peroxide compound comprises 4% to 12% hydrogen peroxide and 3% to about 20% carbamide peroxide.

24. The method of claim 1, wherein one of the first component and the second component includes 5% to about 25% of glycerin, and wherein the at least one gelling agent is form 1% to about 40%.

* * * * *